(12) United States Patent
Gartside et al.

(10) Patent No.: US 7,214,841 B2
(45) Date of Patent: May 8, 2007

(54) PROCESSING C4 OLEFIN STREAMS FOR THE MAXIMUM PRODUCTION OF PROPYLENE

(75) Inventors: Robert J. Gartside, Summit, NJ (US); Marvin I. Greene, Wayne, NJ (US)

(73) Assignee: ABB Lummus Global Inc., Bloomfield, NJ (US)

( * ) Notice: Subject to any disclaimer, the term of this patent is extended or adjusted under 35 U.S.C. 154(b) by 270 days.

(21) Appl. No.: 10/620,186

(22) Filed: Jul. 15, 2003

(65) Prior Publication Data
US 2005/0014981 A1 Jan. 20, 2005

(51) Int. Cl.
*C07C 6/04* (2006.01)
(52) U.S. Cl. .................... 585/324; 585/644; 585/646
(58) Field of Classification Search ............ 585/324, 585/644, 646
See application file for complete search history.

(56) References Cited

U.S. PATENT DOCUMENTS

| | | | |
|---|---|---|---|
| 5,087,780 A | 2/1992 | Arganbright | 585/259 |
| 5,898,091 A | 4/1999 | Chodorge et al. | 585/647 |
| 6,075,173 A | 6/2000 | Chodorge et al. | 585/324 |
| 6,271,430 B2 * | 8/2001 | Schwab et al. | 585/644 |
| 6,358,482 B1 | 3/2002 | Chodorge et al. | 422/189 |
| 6,580,009 B2 | 6/2003 | Schwab et al. | 585/324 |
| 6,777,582 B2 | 8/2004 | Gartside et al. | 585/324 |

OTHER PUBLICATIONS

PCT International Search Report and Written Opinion for PCT/US2004/022118.

* cited by examiner

*Primary Examiner*—Thuan Dinh Dang
(74) *Attorney, Agent, or Firm*—Alix, Yale & Ristas, LLP (57) ABSTRACT

In order to maximize the production of propylene when the external supply of ethylene is limited, the $C_4$ cut from a hydrocarbon cracking process is first subjected to autometathesis prior to any isobutylene removal and without any ethylene addition. This favors the reactions which produce propylene and pentenes. The ethylene and propylene produced are then removed leaving a stream of the $C_4$'s and heavier components. The $C_5$ and heavier components are then removed leaving a mixture of 1-butene, 2-butene, isobutylene, and iso- and normal butanes. The isobutylene is next removed preferably by a catalytic distillation hydroisomerization de-isobutyleneizer. The isobutylene-free $C_4$ stream is then mixed with the product ethylene removed from the autometathesis product together with any fresh external ethylene needed and subjected to conventional metathesis producing additional propylene.

22 Claims, 2 Drawing Sheets

PROCESSING C4 OLEFIN STREAMS FOR THE MAXIMUM PRODUCTION OF PROPYLENE

BACKGROUND OF THE INVENTION

The present invention relates to the processing of a $C_3$ to $C_6$ hydrocarbon cut from a cracking process, such as steam or fluid catalytic cracking, primarily for conversion of $C_4$ olefins to propylene via metathesis.

In typical olefin plants, there is a front-end demethanizer for the removal of methane and hydrogen followed by a deethanizer for the removal of ethane, ethylene and $C_2$ acetylene. The bottoms from this deethanizer tower consist of a mixture of compounds ranging in carbon number from $C_3$ to $C_6$. This mixture is separated into different carbon numbers typically by fractionation.

The $C_3$ cut, primarily propylene, is removed as product and is ultimately used for the production of polypropylene or for chemical synthesis such as propylene oxide, cumene, or acrylonitrile. The methyl acetylene and propadiene (MAPD) impurities must be removed either by fractionation or hydrogenation. Hydrogenation is preferred since some of these highly unsaturated $C_3$ compounds end up as propylene thereby increasing the yield.

The $C_4$ cut consisting of $C_4$ acetylenes, butadiene, iso- and normal butenes, and iso- and normal butane can be processed in many ways. A typical steam cracker $C_4$ cut contains the following components in weight %:

| | |
|---|---|
| $C_4$ acetylenes | trace |
| butadiene | 33% |
| 1-butene | 15% |
| 2-butene | 9% |
| isobutylene | 30% |
| iso- & normal butane | 13% |

Typically, the butadiene and $C_4$ acetylenes are removed first. This can be accomplished by either hydrogenation or extraction. If extraction is employed, the remaining 1-butene and 2-butene remain essentially in the same ratio as that of the initial feedstock. If hydrogenation is employed, the initial product from butadiene hydrogenation is 1-butene. Subsequently, hydroisomerization occurs within the same reaction system changing the 1-butene to 2-butene. The extent of this reaction depends upon catalyst and reaction conditions within the hydrogenation system. However, it is common practice to limit the extent of hydroisomerization in order to avoid "over hydrogenation" and the production of butanes from butenes. This would represent a loss of butene feedstock for subsequent operations downstream. The butenes remaining in the mixture consist of normal olefins (1-butene, 2-butene) and iso-olefins (isobutylene). The balance of the mixture consists of both iso- and normal butanes from the original feed plus what was produced in the hydrogenation steps and any small quantity of unconverted or unrecovered butadiene.

The butenes have many uses. One such use is for the production of propylene via metathesis. Another is for the production of ethylene and hexene via metathesis. Conventional metathesis involves the reaction of normal butenes (both 1-butene and 2-butene) with ethylene. These reactions occur in the presence of a catalyst which consists of a group VIA or VII A metal oxide either supported or unsupported. Typical catalysts for metathesis are tungsten oxide supported on silica or rhenium oxide supported on alumina. Isobutylene (isobutene) is typically removed from the feedstock prior to the metathesis reaction step. The reaction of isobutylene with ethylene is non-productive and reaction with itself and/or other $C_4$'s is limited in the presence of excess ethylene. Non-productive reactions essentially occupy catalyst sites but produce no product. If allowed to remain in the feed to the metathesis unit, the concentration of this non-reactive species would build up creating capacity limitations. The reaction of 1-butene with ethylene is also non-productive. However, it is common to employ a double bond isomerization catalyst within the metathesis reactor to shift 1-butene to 2-butene and allow for continued reaction. Typical double bond isomerization catalysts include basic metal oxides (Group IIA) either supported or unsupported. Magnesium oxide or calcium oxide are examples of such double bond isomerization catalysts that are physically admixed with the metathesis catalyst. No equivalent co-catalyst exists for the skeletal isomerization of isobutylene to normal butene. In the case of the conventional metathesis system employing both a metathesis catalyst and a co-mixed double bond isomerization catalyst, the butadiene must be removed to a level of less than 500 ppm to avoid rapid fouling of the double bond isomerization catalyst. The metathesis catalyst itself can tolerate butadiene levels up to 10,000 ppm.

It is common to employ an isobutylene removal step prior to metathesis. Options include reacting it with methanol to produce methyl tertiary butyl ether (MTBE) or separating the isobutylene from the butenes by fractionation. In U.S. Pat. No. 6,358,482, the inventors teach the removal of isobutylene from the $C_4$ mixture prior to metathesis. This scheme is further reflected in U.S. Pat. Nos. 6,075,173 and 5,898,091. In other prior art, in U.S. Pat. No. 6,580,009, Schwab et al teach a process for the production of propylene and hexene from a limited ethylene fraction. For molar ratios of ethylene to butenes (expressed as n-butenes) from 0.05 to 0.60, the inventors utilize a raffinate II stream as the $C_4$ feedstock. A raffinate II stream is by definition a stream following isobutylene removal. Further, in claim 6 of the published application, they teach the steps of: (1) removal of butadiene; (2) removal of isobutylene by various means; (3) removal of the oxygenate impurities; (4) metathesis of the resultant raffinate II stream with 0.05 to 0.6 molar ratio of ethylene; (5) separation of products to form a lighter fraction of $C_2$ and $C_3$ stream and a heavier fraction $C_4$ to $C_6$ stream; (6) separating the lighter fraction into $C_2$ and $C_3$ product streams; (7) separating the heavier stream into a $C_4$ stream, an intermediate $C_5$ stream and a heavier $C_6+$ stream; and (8) recycle of the unreacted $C_4$ and at least partially the $C_5$ normal olefins. This process specifically removes the isobutylene prior to metathesis.

In U.S. Pat. No. 6,271,430, Scwab et al disclose a two-step process for the production of propylene. The first step consists of reacting 1-butene and 2-butene in a raffinate II stream in an autometathesis reaction to form propylene and 2-pentene. The products are then separated in the second step. The third step reacts specifically the 2-pentene with ethylene to form propylene and 1-butene. This process utilizes the isobutylene free raffinate II stream. The pentenes recycled and reacted with ethylene are normal pentenes (2-pentene).

It is known that isobutylene removal from the $C_4$ stream can also be accomplished by employing a combined catalytic distillation hydroisomerization deisobutyleneizer system (CD DIB system). This system will both remove the isobutylene and recover n-butenes at high efficiency by isomerizing the 1-butene to 2-butene with known isomerization catalysts and thus increase the volatility difference. This technology combines conventional fractionation for isobutylene removal with hydroisomerization within a catalytic distillation tower. In U.S. Pat. No. 5,087,780 to Arganbright, 2-butene is hydroisomerized to 1-butene as the fractionation occurs. This allows greater than equilibrium amounts of 1-butene to be formed as the mixture is separated. Similarly, 1-butene can be hydroisomerized to 2-butene in a catalytic distillation tower. In separating a $C_4$ stream containing isobutylene, 1-butene, and 2-butene (plus paraffins), it is difficult to separate isobutylene from 1-butene since their boiling points are very close. By employing simultaneous hydroisomerization of the 1-butene to 2-butene with fractionation of isobutylene (CD DIB), isobutylene can be separated from the normal butenes at high efficiency.

The metathesis reaction described above is equimolar, i.e., one mol of ethylene reacts with 1 mol of 2-butene to produce 2 mols of propylene. However, commercially, in many cases, the quantity of ethylene available is limited with respect to the quantity of butenes available. In addition, the ethylene is an expensive feedstock and it is desired to limit the quantities of ethylene used. As the ratio of ethylene to butenes is decreased, there is a greater tendency for the butenes to react with themselves which reduces the overall selectivity to propylene.

The metathesis catalysts and the double bond isomerization catalysts are quite sensitive to poisons. Poisons include water, $CO_2$, oxygenates (such as MTBE), sulfur compounds, nitrogen compounds, and heavy metals. It is common practice to employ guard beds upstream of the metathesis reaction system to insure the removal of these poisons. It does not matter if these guard beds are directly before the metathesis reaction system or further upstream as long as the poisons are removed and no new poisons are subsequently introduced.

Metathesis reactions are very sensitive to the location of the olefin double bond and the stereo-structure of the individual molecules. A pair of olefins adsorb on the surface and exchange double bond positions with the carbon groups on either sides of the double bonds. Metathesis reactions can be classified as productive, half productive or non-productive. As described above, non-productive reactions result in essentially no reaction taking place. When the double bonds shift with metathesis reaction, the new molecules are the same as the originally adsorbed molecules thus no productive reaction occurs. This is typical for reactions between symmetric olefins or reactions between ethylene and alpha olefins. If fully productive reactions occur, new products are generated no matter which orientation the molecules occupy the sites. The reaction between ethylene and 2-butene to form two propylene molecules is a fully productive reaction. Half productive reactions are sterically inhibited. If the pair of olefins adsorb in one orientation, when the double bonds shift new products are formed. Alternately if they adsorb in a different steric configuration, when the bonds shift, the identical olefins are formed and thus no new products are formed. The various metathesis reactions proceed at different rates (a fully productive reaction is usually faster than a half productive reaction) and with different weight selectivities to propylene. Table A summarizes the reactions between ethylene and various butenes and the reactions between the butenes themselves.

The reactions listed represent the base reaction with ethylene (reaction 1, 4 and 5) as well as the reactions between the various $C_4$ olefins. It is especially important to make a distinction between the selectivity to propylene from total $C_4$ olefins (including isobutylene) and the selectivity to propylene from the normal $C_4$ olefins involved in the reaction. The reaction of isobutylene with 2-butene (reaction 6) produces propylene and a branched $C_5$ molecule. For this reaction, propylene is produced at 37.5 weight % selectivity from total $C_4$'s (similar to reaction 2) but at a 75 weight % selectivity from normal $C_4$'s (2-butene). For the purposes of definitions, conventional metathesis is defined as the reaction of the $C_4$ olefin stream with ethylene. However, the $C_4$ stream can also react without the presence of ethylene as a feedstock. This reaction is called auto or self metathesis. In this case, reactions 2,3 6, and 7 are the only possible reactions and will occur at rates dependent upon the feedstock composition.

TABLE A

| | Reaction | Rate | Wt % selectivity ($C_3H_6$ from total C4's) | Wt % selectivity $C_3H_6$ from (n-C4's) |
|---|---|---|---|---|
| 1 | 2-butene + ethylene → 2 propylene (conventional metathesis) (fully productive) | Fast | 100 | 100 |
| 2 | 1-butene + 2-butene → propylene + 2-pentene (fully productive) | Fast | 37.5 | 37.5 |
| 3 | 1-butene + 1-butene → ethylene + 3-hexene (half productive) | Slow | 0 | 0 |
| 4 | isobutylene + ethylene → no reaction | No Rkn | | |
| 5 | 1-butene + ethylene → no reaction | No Rkn | | |
| 6 | isobutylene + 2-butene → propylene + 2-Me 2-butene (fully productive) | Fast | 37.5 | 75 |
| 7 | isobutylene + 1-butene → ethylene + 2-me 2-pentene (half productive) | Slow | 0 | 0 |

It is common practice in conventional metathesis to maximize reaction 1 to produce propylene. This will maximize the selectivity to propylene. As such, excess ethylene is used to reduce the extent of the reactions of butenes with themselves (reactions 2, 3, 6, and 7). The theoretical ratio is 1/1 molar or 0.5 weight ratio of ethylene to n-butenes but it is common in conventional metathesis to employ significantly greater ratios, typically, 1.3 or larger molar ratio to minimize reactions 2, 3, 6 and 7. Under conditions of excess ethylene, and due to the fact that both isobutylene and 1-butene do not react with ethylene (see reactions 4 and 5), two process sequences are employed. First, the isobutylene is removed prior to metathesis. If isobutylene is not removed, it will build up as the n-butenes are recycled to achieve high yield. Second, 1-butene is isomerized to 2-butene by including a double bond isomerization catalyst such as magnesium oxide admixed with the metathesis catalyst. Note that this catalyst will not cause skeletal isomerization (isobutylene to normal butylenes) but only shift the double bond from the 1 position to the 2 position. Thus by operating with excess ethylene, eliminating isobutylene from the metathesis feed prior to reaction, and employing a double bond isomerization catalyst, reaction 1 is maximized.

When there is limited or no fresh ethylene (or excess butylenes for the ethylene available), there are currently two options available for propylene production. In these cases, the current technology will first remove the isobutylene and then process the normal butenes with whatever ethylene is available. The entire n-butenes only mixture is subjected to metathesis with the available ethylene. Ultimately, if there is no fresh ethylene available, the $C_4$'s react with themselves (auto metathesis). Under low ethylene conditions, reactions 2, 3, 6 and 7 will occur, all leading to a lower propylene selectivity (37.5% or lower versus 100% for reaction 1). The lower selectivity results in lower propylene production. Note that reactions 6 and 7 will be minimized as a result of the removal of isobutylene (to low levels but not necessarily zero). Alternately, the molar flows of ethylene and butenes can be matched by limiting the flow of butenes to produce conditions where there is a high selectivity of the normal butenes to propylene via reaction 1. By limiting the flow of n-butenes to match ethylene, the production of propylene is limited by the reduced butenes flow.

Pentenes and some hexenes are formed to some extent in the conventional metathesis case with low ethylene. The volume of these components will depend upon the ethylene/n-butenes ratio with a lower ratio producing more $C_5$ and $C_6$ components. In the conventional prior art case where isobutylene is removed before any metathesis, these $C_5$ and $C_6$ olefins are normal olefins since no skeletal isomerization occurs. It is possible to recycle these olefins back to the metathesis step where for example the reaction with ethylene and 2-pentene will occur yielding propylene and 1-butene. The 1-butene is recovered and recycled. Note however, with limited ethylene, reaction 1 can occur only to the limit of the ethylene availability. Ultimately these non-selective byproducts, pentenes and hexenes, must be purged from the system. While the presence of these olefins impacts the required size of the equipment, they do not represent losses of potential propylene production.

SUMMARY OF THE INVENTION

An object of the present invention is to maximize the production of propylene when processing a $C_4$ cut from a hydrocarbon cracking process when the supply of ethylene is limited and when the $C_4$ cut contains high isobutylene and isobutane levels. The $C_4$ stream has had butadiene removed to a level where the inlet concentration is <10,000 ppm. This stream is commonly called a Raffinate I. The invention involves a first step (1) of subjecting the entire $C_4$ cut to autometathesis prior to any isobutylene removal. In this step, reactions 2, 3, 6 and 7 set forth above occur with fully productive reactions 2 and 6, that produce propylene and either n-pentenes or iso-pentenes, predominating. There is no ethylene used as feedstock in this step. In step (2) any product ethylene (from reactions 3 and 7) is removed. In step (3) product propylene is removed. The resultant stream consists of $C_4$'s and heavier components. In step (4) the $C_5$ and heavier components are removed leaving a mixture of butenes (1-butene, 2-butene and isobutylene) and both iso- and normal butanes. The isobutylene is next removed from this $C_4$ stream in step (5) and the resultant isobutylene-free $C_4$ stream is mixed with the available fresh ethylene plus any produced ethylene from the autometathesis step. This isobutylene free $C_4$ stream, admixed with ethylene, is then subjected to conventional metathesis in step (6) producing additional propylene and maximizing reaction 1.

Overall, since reaction 1 has the highest propylene selectivity, it is desired to fully maximize this reaction. Under conditions of low ethylene, butenes will react with each other. This will not only produce propylene at lower selectivity, it consumes two butenes (rather than one as in reaction 1). By allowing reaction of normal butenes with isobutylene (in addition to other normal butenes) in the first autometathesis step, the conversion of n-butenes to propylene proceeds at higher selectivity (from n-butenes) and isobutylene is removed by reaction not fractionation. In the second conventional metathesis step, the remaining n-butenes only are reacted at maximum selectivity with ethylene. Since some of the normal butenes have been removed via the autometathesis reaction (step 1), the reaction proceeds using higher ethylene/butenes ratios than would be possible if the entire feed were processed with that same limited amount of ethylene as in the prior art.

In step (4) above, the $C_5$ and heavier components (pentenes and hexenes) are removed from the $C_4$ and heavier mixture. In this case, as opposed to the system of the prior art, these $C_5$ and $C_6$ olefins consist of both normal olefins and iso-olefins. The iso-olefins are formed via reactions 6 and 7 while the normal olefins are formed via reactions 2 and 3. If the majority of the iso-olefins are not removed and are allowed to react with ethylene in the conventional metathesis step 6, isobutylene would be reformed via the reverse of reaction 7. This reaction will consume ethylene with no propylene production. The net effect will be to minimize the beneficial effect of the autometathesis isobutylene reaction on propylene selectivity and additionally eliminate any isobutylene removal capacity advantages since essentially all isobutylene removed by reaction in step 1 would be reformed in step 6.

DESCRIPTION OF THE PREFERRED EMBODIMENT

Before describing the present invention in detail, a typical prior art system for the production of propylene from a $C_4$ hydrocarbon stream from a cracking process will be described with reference to FIG. 1. In this way, it can be better seen how the present invention differs and increases the production of propylene.

Figure 1:
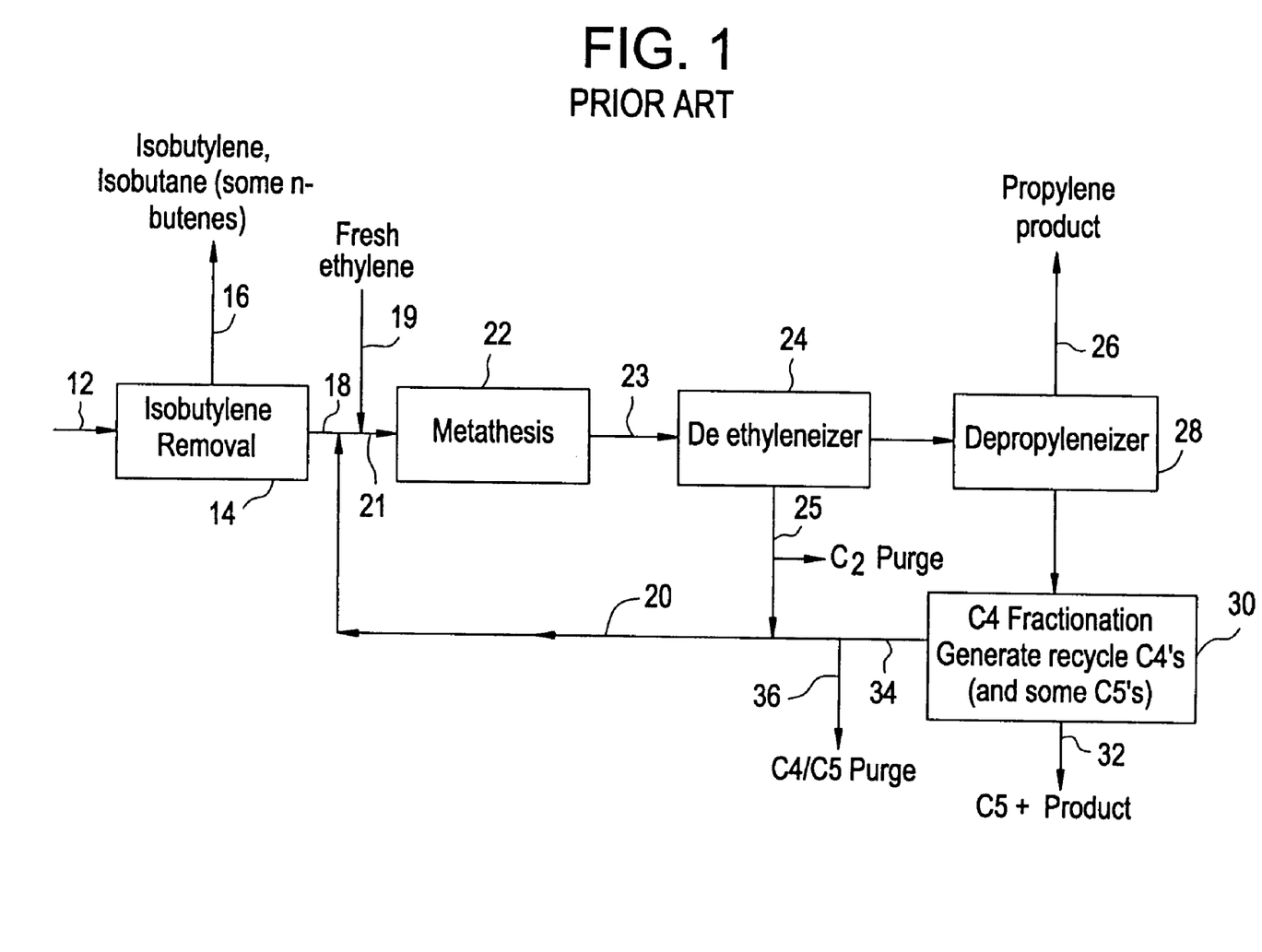
FIG. 1 is a flow diagram of a prior art system for processing a $C_4$ olefin stream for propylene production.

As shown in FIG. 1, the $C_4$ cut feed stream 12 is fed to the isobutylene removal step 14. This $C_4$ stream has had butadiene removed to a level consistent with the catalyst system employed. If a double bond isomerization catalyst is utilized, then the butadiene is <500 ppm. The $C_4$ cut is typically as previously described and the current options for the removal of the isobutylene are as follows:

1. Selectively react isobutylene with methanol to form methyl tertiary butyl ether (MTBE).
2. Selectively react isobutylene with itself to form isooctenes.
3. Fractionation in a de-isobutyleneizer to remove both isobutylene and isobutane.
4. Treatment in a combined hydroisomerization de-isobutyleneizer catalytic distillation system (CD DIB system) for fractionation to remove both isobutylene and isobutane combined with hydroisomerization of 1-butene to 2-butene to maximize the 2-butene content.

Isobutane and some of the n-butenes may also be removed along with the isobutylene at 16. The remaining $C_4$ stream 18 along with the recycle $C_4$ stream 20 is subjected to conventional metathesis at 22. Fresh ethylene 19 along with unreacted ethylene and some product ethylene from separation step 24 as stream 25 is combined to generate the feed 21 to the conventional metathesis step 22. It is common but not required to include a double bond isomerization catalyst admixed with the metathesis catalyst to convert 1-butene to 2-butene. In the metathesis process 22, reactions 2, 3, 6 and 7 occur leading to a propylene selectivity of 37.5% or less. Reaction 1 will also occur to a greater or lesser extent dependent upon the concentration of ethylene. The metathesis effluent 23 in the prior art process then continues with ethylene recycle 25 removal at 24, propylene product 26 removal at 28 and $C_4$ fractionation at 30 to remove most of the $C_5$+ constituents 32. The remaining stream 34 contains primarily n-butenes and n-butanes with some $C_5$ and heavier components. In order to prevent the build up of unreactive butanes and the residual $C_5$ and heavier components in the recycle stream, a portion of the stream 34 is purged at 36. The remaining stream 20 is recycled to the metathesis step 22.

Figure 2:
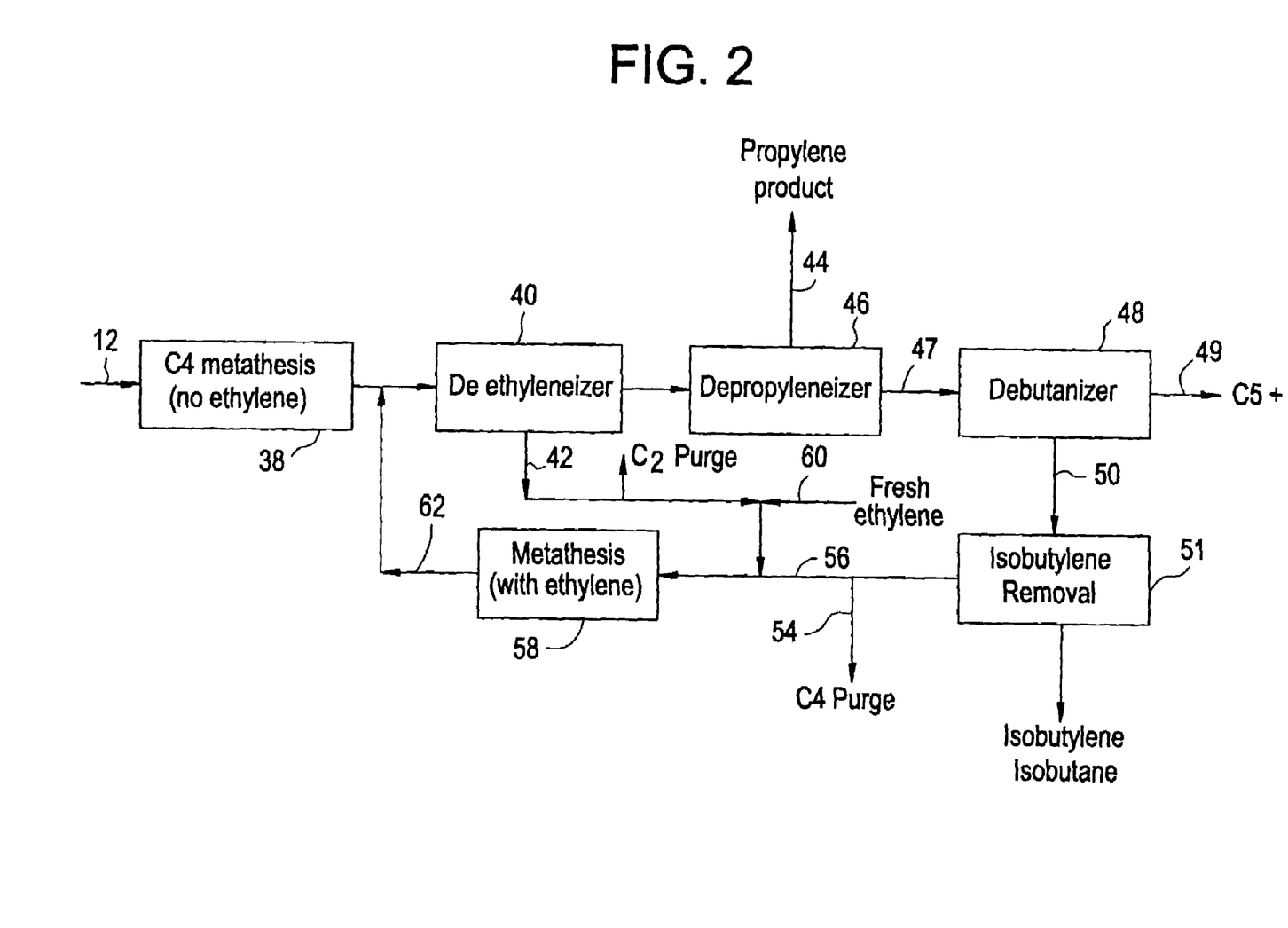
FIG. 2 is a flow diagram of the system of the present invention for processing a $C_4$ olefin stream to maximize the production of propylene.

In the present invention, shown in FIG. 2, involving metathesis without fresh ethylene or at low fresh ethylene levels, an initial autometathesis step is purposely utilized. Isobutylene can be reacted with the other normal butenes and isobutylene conversions can reach 50 or 60%. The products from the reaction with 1-butene according to reaction 7 are ethylene and 2-methyl 2-pentene while the products with 2-butene according to reaction 6 are propylene and 2-methyl 2-butene. These autometathesis reactions can be utilized in combination with a second conventional metathesis reaction system and a different fractionation/ isobutylene removal sequence to maximize propylene production from the entire butenes stream.

Under those cases where the molar ratio of ethylene to the $C_4$ stream is zero or less than 0.5 weight ratio or 1.0 molar ratio, the $C_4$ stream is processed more efficiently and the total propylene made from a steam cracker or fluid catalytic cracker $C_4$ stream that contains isobutylene and isobutane can be increased according to the present invention by first employing an autometathesis step followed by an isobutylene removal system downstream of the metathesis reaction instead of upstream of the metathesis reaction as is commonly practiced in the prior art. Then, a second conventional metathesis reaction system is used where ethylene is reacted with the recycle $C_4$ stream following the isobutylene removal. It is preferred that the pentenes be removed prior to the $C_4$ recycle to the second metathesis reaction system.

Referring to FIG. 2, mixed $C_4$ feedstock 12 containing both normal butenes and iso-butylenes along with paraffins is fed to an autometathesis reaction step 38. This allows only reactions 2, 3, 6 and 7 to occur. Reactions 2 and 6 will predominate since they are faster reactions. This will produce propylene and both n-pentenes and iso-pentenes. Importantly, to the extent that isobutylene is present and reacts via reaction 6, the selectivity of propylene from the n-butenes is 75% instead of 37.5% as it would be via reaction 2 or zero as it would be via reaction 3. Further, to the extent that reaction 7 occurs with isobutylene, ethylene product from the autometathesis is available for recycle. While there is no requirement for feed composition ratios, it is preferred that the ratio of 2-butene to the sum of 1-butene and isobutylene is near 1 in order to maximize conversions in this auto metathesis step. In this case, a double bond isomerization catalyst is not necessarily used in combination with the metathesis catalyst. Since the hydrogenation reactions used to remove the butadiene to low levels also promote hydroisomerization of 1-butene to 2-butene, the above-mentioned ratio of 2-butene to the sum of 1-butene and isobutylene is easier to obtain under conditions where some butadiene leakage from the hydrogenation step is allowed and butadiene levels are >500 ppm.

Following the autometathesis reaction at 38, a recycle stream 62 is added (to be explained later) and ethylene 42 comprising any product or unreacted ethylene is removed at 40. This ethylene 42 is available for use later in the process. The ethylene removal at 40 is followed by separation of the propylene product 44 at 46. The $C_4$ and heavier effluent 47 from the propylene separation step 46 is then separated into a $C_4$ stream 50 and a $C_5$+ stream 49. This occurs in a debutanizer 48. If high concentrations of the $C_5$ and heavier components were allowed to remain, the isopentenes formed by reaction with isobutylene in the autometathesis step could be subsequently reacted with ethylene. Isobutylene would be re-formed by reaction with feed ethylene and/or product propylene by the reverse of reactions 6 and 7. Note, however, that to the extent that the normal pentenes are allowed to pass to the conventional metathesis, they react to form propylene and normal butenes which is a desirable reaction. At this point, there is a mixture of n-butenes, isobutylene, and both iso and normal butanes and some $C_5$ and heavier material.

Alternately, the steps of propylene separation 46 and $C_4$ separation can occur in a single step. A single fractionation tower can be utilized where the overhead product is the propylene product 44, the bottoms product is the $C_5$+ stream 49 and the $C_4$ stream 50 is removed as a side draw for the tower.

The $C_4$ stream 50 contains the unreacted normal butenes (1-butene and 2-butene) and any unreacted iso-butylenes. This is then sent to the isobutylene removal operation 51. Importantly, the total isobutylene flow to the isobutylene removal operation has been reduced because a large fraction of the butenes, about 50% to 60% depending on the single pass conversion, has been converted to either propylene or $C_5$'s and removed from the feed prior to the isobutylene removal 51. Thus, the requirements for the isobutylene and isobutane removal step are considerably reduced as compared to processing the entire iso $C_4$ flow as would be the case where the isobutylene is removed prior to metathesis.

The isobutylene removal avoids unproductive metathesis reaction with ethylene in the following process step. The options include the four isobutylene removal processes previously identified. With respect to the process involving the reaction with methanol to produce MTBE, only isobutylene is removed. Since isobutane is not removed, it must be purged downstream along with the purge of n-butanes at 54. This is also true of the removal technique where isobutylene is reacted with itself to form isooctenes. In these case, the purge will contain normal butenes as well thus limiting the propylene production as a result of the loss of normal butene feed. Using a de-isobutyleneizer to remove the isobutylene by fractionation also removes the isobutane. This reduces the volume of the recycle and purge thereby increasing the $C_4$ utilization.

The preferred option for removing the isobutylene at 51 is the previously described hydroisomerization de-isobutyleneizer catalytic distillation tower (CD DIB tower). This not only removes both isobutane and isobutylene but it also isomerizes 1-butene to 2-butene. This maximizes the recovery of the n-butenes, by minimizing the 1-butene that is lost with the isobutylene in the overhead product, and it produces all or most of the n-$C_4$'s recovered as a bottom product from the tower as 2-butene. This will maximize propylene selectivity in the next process step.

Following the isobutylene removal step at 51 and any required purge at 54, the isobutylene free stream 56 is subjected to conventional metathesis with ethylene at 58. The ethylene is a combination of the ethylene that may have been produced in the autometathesis step 38 by reactions 3 and 7 and removed at 42 and the limited amount of fresh ethylene 60 available. The reaction between ethylene and 2-butene proceeds rapidly and at high selectivity as described above in reaction 1 for conventional metathesis. With the limited ethylene, by removing the isobutylene, the reactions proceed more efficiently. Further, for the case where 2-butene is maximized by employing a hydroisomerization de-isobutyleneizer catalytic distillation tower, the propylene selectivity is maximized via reaction 1. The effluent 62 from the conventional metathesis reaction at 58 is combined and processed with the effluent from the first autometathesis reaction at 38.

Listed below are various examples for processing a $C_4$ stream consisting of 18,625 kg/hr of a $C_4$ stream of the following composition in mol percent:

| | |
|---|---|
| i-butane | 28.38% |
| n-butane | 16.42% |
| trans 2-butene | 14.09% |
| cis 2-butene | 8.89% |
| 1-butene | 12.53% |
| Butadiene | 0.81% |
| isobutylene | 18.64% |
| other | 0.24% | isobutylene as % of total butenes = 33.9%
2-butene/(1-butene + iso-butylene) = 22.98/31.17 = 0.73

In these examples, several different levels of ethylene are considered as follows:

In the first case, 2750 kg/hr ethylene is available as fresh feed. This represents a high ethylene/normal butenes weight ratio of 0.41.

In the second case, 1375 kg/hr of fresh ethylene is available. This is a reduced, moderate weight ratio of 0.21.

In the third case, only 590 kg/hr of fresh ethylene is available. This is a low weight ratio of 0.09.

Production material balances will be defined for each of these cases comparing both the conventional processing scheme where isobutylene is removed prior to metathesis and the processing scheme of the present invention.

FIG. 1—EXAMPLE 1

Conventional Processing with High Ethylene

In this case 2750 kg/hr fresh ethylene is available for a n-butene flow of 6651 kg/hr. This is a 0.41 weight ratio or a 0.85 fresh feed molar ratio. The material balance is summarized in Table B.

Step 1. The $C_4$ feed is first sent to a Catalytic Distillation DIB tower 14 where 9054 kg/hr of isobutylene and isobutane is removed as overheads 16. The bottom product 18 (9570 kg/hr) is essentially a pure 2-butene stream mixed with paraffins.

Step 2. The bottom stream 18 is mixed with a combination of fresh ethylene 19 and recycle ethylene from the deethyleneizer 24 and the recycle 34 from the $C_4$ fractionation system 30 (after purge 36) and fed to the metathesis unit 22. The metathesis unit contains both a metathesis and a double bond isomerization catalyst. There is a once through 59% normal butene conversion and the molar selectivity to propylene is 99%. Selectivity is defined as the mols of propylene produced per mols of ethylene and n-butenes consumed. Note that the conversion of the small amount of isobutylene is low due to excess ethylene.

Step 3. The ethylene is separated in the deethyleneneizer 24 and recycled for high utilization (98%). 3981 kg/hr of product ethylene, which is purged to remove the small amount of ethane contained in the fresh ethylene stream, is then combined with the 2750 kg/hr of fresh ethylene 19 for feed to the metathesis reactor 22.

Step 4. A total of 8163 kg/hr propylene product (containing 8145 kg/hr propylene) is recovered as the overhead 26 from the depropyleneizer 28.

Step 5. Before recycle, the $C_4$ stream 29 is fractionated at 30 to remove some of the $C_5$'s and all of the heavier materials. It is not necessary to remove all the $C_5$'s from the $C_4$ stream since they can be recycled as described above. Following fractionation at 30, the remaining $C_4$ stream 34 has a purge 36 to eliminate $C_4$ paraffins from the metathesis loop. The $C_4$'s are recycled to achieve a high utilization (88%) and this dilutes the feed considerably with paraffins. Paraffins are 49% by weight of the metathesis unit feed and 60% of the $C_4$'s to that unit.

TABLE B

| | $C_4$ Feed Stream 12 Kg/H | Isobutylene Removal 16 Kg/H | Conventional Metathesis Feed 21 Kg/H | Metathesis Effluent 23 Kg/H | Ethylene Product 25 Kg/H | Propylene Product 26 Kg/H | $C_4$ Purge 36 Kg/H |
|---|---|---|---|---|---|---|---|
| $C_2$ | 0.0 | 0.0 | 6656.2 | 3977.4 | 3975.8 | 1.6 | 0.0 |
| $C_3$ | 0.0 | 0.0 | 18.6 | 8166.8 | 6.0 | 8145.2 | 2.9 |
| Inerts (Butane + Pentane) | 8557.6 | 5469.3 | 16521.1 | 16521.1 | 0.0 | 11.3 | 3046.1 |
| n-$C_4$ | 6507.8 | 134.9 | 9422.6 | 3821.6 | 0.0 | 3.9 | 704.4 |
| i-$C_4$ | 3416.0 | 3321.4 | 374.4 | 345.6 | 0.0 | 1.3 | 63.5 |
| BD | 143.4 | 129.1 | 75.8 | 75.8 | 0.0 | 0.2 | 13.9 |
| n-$C_5$ | 0.0 | 0.0 | 457.4 | 560.8 | 0.0 | 0.0 | 103.5 |
| i-$C_5$ | 0.0 | 0.0 | 95.8 | 117.4 | 0.0 | 0.0 | 21.7 |
| n-$C_6$ | 0.0 | 0.0 | 76.1 | 93.3 | 0.0 | 0.0 | 17.2 |

TABLE B-continued

| | $C_4$ Feed Stream 12 Kg/H | Isobutylene Removal 16 Kg/H | Conventional Metathesis Feed 21 Kg/H | Metathesis Effluent 23 Kg/H | Ethylene Product 25 Kg/H | Propylene Product 26 Kg/H | $C_4$ Purge 36 Kg/H |
|---|---|---|---|---|---|---|---|
| i-$C_6$ | 0.0 | 0.0 | 74.8 | 91.7 | 0.0 | 0.0 | 16.9 |
| $C_6$+ | 0.0 | 0.0 | 5.1 | 6.3 | 0.0 | 0.0 | 1.2 |
| SUM | 18624.8 | 9054.7 | 33777.7 | 33777.7 | 3981.8 | 8163.5 | 3991.3 |

It is to be noted that the listings in this Table B as well as the following tables for $C_2$, $C_3$, n-$C_4$, i-$C_4$, n-$C_5$, i-$C_5$, n-$C_6$, i-$C_6$ all refer to olefins. The BD listing is the diolefin butadiene and all paraffins for the $C_4$ and $C_5$ fractions including iso- and normal paraffins are grouped as inerts.

FIG. 1—EXAMPLE 2

Conventional Moderate Ethylen

In the second example, half the ethylene is available (1375 kg/hr fresh ethylene). This represents an ethylene to n-butenes ratio of 0.21 wt fraction or 0.43 mol fraction. The material balance is summarized in Table C.

Step 1. This is identical to example 1 and 9570 kg/hr (18,624 minus 9054) of feed is created for the conventional metathesis unit.

Step 2. With reduced ethylene, the selectivity to propylene is reduced. The molar selectivity drops to 88.8% from 99%. The ethylene conversion is higher (66 vs 40%) and the butene conversion is lower (36.5 vs 59) under these conditions.

Step 3. The ethylene is recovered and recycled.

Step 4. The propylene is recovered. As a result of the lower ethylene flow, the propylene production is reduced to 5110 kg/hr from 8164 kg/hr. A drop of 37%.

Step 5. The unreacted $C_4$'s are recycled along with a substantial portion of the $C_5$'s produced by the lower selective reactions. The combination of lower conversion and the desire for high butene utilization creates very large recycles. The total metathesis reactor flow increases from 33777 kg/hr to 43883 (a factor of 1.3). In order to limit the inert concentration to approximately 60% of the $C_4$ stream and thus avoid excessive capital and energy costs, purging is increased and the overall utilization of butenes decreases (79% versus 88%).

FIG. 1—EXAMPLE 3

Conventional Low Ethylene

In this final example for the conventional case, the fresh ethylene is almost zero (590 kg/hr). This represents a fresh ethylene/n-butenes of 0.08 weight ratio or 0.18 molar ratio. The material balance is summarized in Table D.

Step 1. This is identical and 9570 kg/hr of a feed is created for the conventional metathesis unit.

Step 2. With still further reduced ethylene, the selectivity to propylene is even worse. The overall molar selectivity drops from 88.8% to 76.8%. This is equivalent to 57.6 wt % selectivity from $C_4$'s. The butene conversion is essentially the same (37.3 vs 36.5 in example 2) under these conditions.

Step 3. The ethylene is recovered and recycled. With the low level of fresh ethylene, this flow is very small.

Step 4. The propylene is recovered. As a result of the very low ethylene flow, the propylene production is reduced to 3521 kg/hr from 5110 kg/hr. This is only 43% of the production of example 1.

Step 5. The unreacted $C_4$'s are recycled along with a substantial portion of the $C_5$'s produced by the lower selective reactions. The combination of lower conversion and the desire for high butene utilization creates very large recycles. The total recycle flow increases from 32379 kg/hr to 36800. This increases the conventional metathesis reactor flow to 47265 kg/hr or 40% more than example 1.

TABLE C

| | $C_4$ Feed Stream 12 Kg/H | Isobutylene Removal 16 Kg/H | Conventional Metathesis Feed 21 Kg/H | Metathesis Effluent 23 Kg/H | Ethylene Product 25 Kg/H | Propylene Product 26 Kg/H | $C_4$ Purge 36 Kg/H |
|---|---|---|---|---|---|---|---|
| $C_2$ | 0.0 | 0.0 | 2033.9 | 687.3 | 685.2 | 2.1 | 0.0 |
| $C_3$ | 0.0 | 0.0 | 23.3 | 5123.4 | 1.0 | 5096.1 | 3.9 |
| Inerts (Butane + Pentane) | 8557.6 | 5469.3 | 20342.6 | 20342.6 | 0.0 | 7.1 | 3050.3 |
| n-$C_4$ | 6507.8 | 134.9 | 13700.1 | 8699.5 | 0.0 | 4.4 | 1304.3 |
| i-$C_4$ | 3416.0 | 3321.4 | 216.8 | 145.2 | 0.0 | 0.2 | 21.7 |
| BD | 143.4 | 129.1 | 93.8 | 93.8 | 0.0 | 0.1 | 14.0 |
| n-$C_5$ | 0.0 | 0.0 | 3936.2 | 4630.8 | 0.0 | 0.0 | 694.6 |
| i-$C_5$ | 0.0 | 0.0 | 152.2 | 179.0 | 0.0 | 0.0 | 26.9 |
| n-$C_6$ | 0.0 | 0.0 | 2374.9 | 2794.0 | 0.0 | 0.0 | 419.1 |
| i-$C_6$ | 0.0 | 0.0 | 424.6 | 499.5 | 0.0 | 0.0 | 74.9 |
| $C_6$+ | 0.0 | 0.0 | 584.9 | 688.1 | 0.0 | 0.0 | 102.5 |
| SUM | 18624.8 | 9054.7 | 43883.2 | 43883.2 | 686.2 | 5110.1 | 5712.4 |

TABLE D

| | C$_4$ Feed Stream 12 Kg/H | Isobutylene Removal 16 Kg/H | Conventional Metathesis Feed 21 Kg/H | Metathesis Effluent 23 Kg/H | Ethylene Product 25 Kg/H | Propylene Product 26 Kg/H | C$_4$ Purge 36 Kg/H |
|---|---|---|---|---|---|---|---|
| C$_2$ | 0.0 | 0.0 | 892.8 | 337.2 | 335.0 | 2.2 | 0.0 |
| C$_3$ | 0.0 | 0.0 | 25.1 | 3540.1 | 0.5 | 3510.7 | 4.3 |
| Inerts (Butane + Pentane) | 8557.6 | 5469.3 | 20355.0 | 20355.0 | 0.0 | 4.9 | 3052.5 |
| n-C$_4$ | 6507.8 | 134.9 | 13503.2 | 8466.4 | 0.0 | 2.9 | 1269.5 |
| i-C$_4$ | 3416.0 | 3321.4 | 169.8 | 89.8 | 0.0 | 0.1 | 13.5 |
| BD | 143.4 | 129.1 | 94.0 | 94.0 | 0.0 | 0.1 | 14.1 |
| n-C$_5$ | 0.0 | 0.0 | 5394.7 | 6346.7 | 0.0 | 0.0 | 952.0 |
| i-C$_5$ | 0.0 | 0.0 | 132.5 | 155.9 | 0.0 | 0.0 | 23.4 |
| n-C$_6$ | 0.0 | 0.0 | 4584.2 | 5393.2 | 0.0 | 0.0 | 809.0 |
| i-C$_6$ | 0.0 | 0.0 | 520.2 | 612.0 | 0.0 | 0.0 | 91.8 |
| C$_6$+ | 0.0 | 0.0 | 1593.8 | 1875.0 | 0.0 | 0.0 | 281.3 |
| SUM | 18624.8 | 9054.7 | 47265.2 | 47265.2 | 335.5 | 3520.9 | 6511.3 |

FIG. 2—EXAMPLE 4 (PRESENT INVENTION)

Moderate Ethylene

In this example for the case of the invention, the fresh ethylene is 1375 kg/hr. This represents a fresh ethylene/n-butenes of 0.21 weight ratio or 0.41 molar ratio. This case is directly comparable to example 2. The material balance is summarized in Table E.

Step 1. The autometathesis 38 (automet) takes place between butene-2 and isobutylene. This results in a high selectivity to propylene via reaction 6. The isobutylene conversion is 57% while the n-butenes conversion is 59%.

Step 2. The product along with recycle 62 goes to the de-ethylenizer 40 where product ethylene from autometathesis as well as unconverted ethylene from the recycle is recovered.

Step 3. Propylene is recovered. The propylene product is 5748 kg/hr. This is 12.5% higher than the propylene production from the conventional case of example 2 (5110 kg/hr) with the same fresh ethylene usage.

Step 4. The depropyleneizer bottoms is sent to a debutanizer 48 where the C$_5$'s 49 are purged. The overhead 50 goes to the isobutylene removal 51.

Step 5. The Catalytic distillation CD-DIB removes the isobutylene remaining and the isobutane. The flow to the de-isobutylene unit 51 is 31114 kg/hr. This is larger than case 2 with the same ethylene flow. However, the isobutylene content is 1625 kg/hr or less than 50% of the fresh feed. Isobutylene content sets the fractionation requirements due to its volatility. The capital and energy costs for this column are reduced in spite of the larger volume flow.

The bottoms is sent to the conventional metathesis reactor along with ethylene after purge to control the paraffin content. Note the total of purge 54 for C$_4$'s plus C$_5$+ 49 is 7452 kg/hr. This compares to 5712 kg/hr for example 2. This increase is the isobutylene reacted to form pentenes in the autometathesis reactor.

Step 6. The conventional metathesis reactor uses ethylene, at a ratio of ethylene to n-butene of 1.70. The ethylene is primarily fresh and recycle ethylene, since little is formed in autometathesis. The ratio is high resulting from the conversion of some of the normal butenes in the autometathesis reactor. Thus propylene is produced at high selectivity by both the high ethylene to n-butenes ratio and the high 2-butene content of the recycle from the CD DIB 51. The effluent is recycled to the deethyleneizer 40 for product recovery.

TABLE E

| | Feed to Automet 38 Kg/H | Automet Product Kg/H | Deethyleneizer Product 42 Kg/H | Propylene Product 44 Kg/H | C$_5$ + 49 Kg/H | Feed to Isobutylene Removal 50 Kg/H | Isobutylene Removed Kg/H | C4 Purge 54 Kg/H | Conventional Metathesis Feed 58 Kg/H | Conventional Metathesis Effluent 62 Kg/H |
|---|---|---|---|---|---|---|---|---|---|---|
| C$_2$ | 0.00 | 295.59 | 2182.79 | 2.05 | 0.00 | 0.00 | 0.00 | 0.00 | 3352.68 | 1889.26 |
| C$_3$ | 0.00 | 1910.51 | 3.28 | 5721.86 | 0.00 | 249.92 | 249.92 | 0.00 | 2.97 | 4064.55 |
| Inerts (Butane + Pentane) | 8557.60 | 8557.60 | 0.00 | 16.34 | 84.47 | 24306.12 | 5876.64 | 2580.1 | 15849.35 | 15849.35 |
| n-C$_4$ | 6507.84 | 2679.24 | 0.00 | 3.01 | 7.57 | 4666.85 | 97.81 | 639.67 | 3929.37 | 1998.18 |
| i-C$_4$ | 3415.97 | 1474.26 | 0.00 | 4.31 | 0.59 | 1625.05 | 1388.79 | 33.08 | 203.19 | 155.69 |
| BD | 143.41 | 143.41 | 0.00 | 0.31 | 0.06 | 161.30 | 140.06 | 2.97 | 18.26 | 18.26 |
| n-C$_5$ | 0.00 | 914.95 | 0.00 | 0.00 | 1158.84 | 64.73 | 0.00 | 171.30 | 1052.27 | 308.62 |
| i-C$_5$ | 0.00 | 1001.37 | 0.00 | 0.00 | 1016.53 | 40.48 | 0.00 | 5.67 | 34.81 | 55.64 |
| n-C$_6$ | 0.00 | 187.53 | 0.00 | 0.00 | 241.49 | 0.01 | 0.00 | 0.00 | 0.01 | 53.97 |
| i-C$_6$ | 0.00 | 1460.18 | 0.00 | 0.00 | 1505.70 | 0.02 | 0.00 | 0.00 | 0.02 | 45.55 |
| C$_6$+ | 0.00 | 0.03 | 0.00 | 0.00 | 3.88 | 0.00 | 0.00 | 0.00 | 0.00 | 3.86 |
| SUM | 18624.8 | 18624.7 | 2186.1 | 5747.9 | 4019.1 | 31114.5 | 7753.2 | 3432.8 | 24442.9 | 24442.9 |

FIG. 2—EXAMPLE 5

Low Ethylene

This is an example of the process of the invention. The available fresh ethylene feed is only 590 kg/hr. This case is directly comparable to example 3 and the material balance is summarized in Table F.

Step 1. There is the same autometathesis reactor. 59% of the n-butenes and 57% of the isobutenes are converted without ethylene. Note that almost 300 kg/hr of ethylene is produced. Again, in the automet reaction, propylene is produced at 44% molar selectivity from all the $C_4$ olefins but at 66.5% from the normal $C_4$ olefins.

Step 2. The ethylene is recovered and recycled.

Step 3. The propylene product 44 is recovered. The total propylene production is 4374 kg/hr. It is significantly greater than the conventional low ethylene case where only 3521 kg/hr is produced with the same ethylene consumption. This represents an increase of 24% compared to the conventional processing scheme of the prior art.

Step 4. The effluent is sent to a debutanizer 48 where the $C_4$ and lighter components are removed overhead for subsequent fractionation and the $C_5+$ components are purged from the system (or recycled to the cracker).

Step 5. The remaining isobutylene and isobutene is removed using a CD DIB in 51. Note that the DIB bottoms feed to the conventional metathesis unit has very little $C_5+$ material.

Step 6. The DIB bottoms is sent to a conventional metathesis unit after purge to control paraffin content. Side reactions are minimized and propylene is produced at high selectivity from the ethylene. The quantity of ethylene is low and is set by the desire to operate this metathesis reaction at a molar ratio of ethylene to n-butenes of 1.7. The effluent is recycled to the feed of the deethylenizer.

The advantages of the invention are as follows:

1. Isobutylene can be processed directly yielding additional propylene. By keeping the iso $C_4$'s in the feed, reactions 2 and 3 are minimized by increasing reactions 6 and 7 and the selectivity of propylene from n-butenes is maximized. Further, the greater quantity of n-olefins are available for conventional metathesis and this can be processed into propylene. This is achieved only if the majority of the $C_5$ isopentenes are removed before the conventional metathesis step.

2. By converting and thus removing a large fraction of the isobutylene via reaction prior to using a hydroisomerization de-isobutyleneizer or other isobutylene removal option, the flow is reduced saving capital cost.

3. By using a hydroisomerization de-isobutyleneizer system (CD DIB) following the reactor, the remaining isobutylene can be separated from the n-butenes thereby maintaining high recovery of 1-butene that would track with the isobutylene in simple fractionation. This also rejects the isobutane and thus reduces recycle quantities. Further, since the normal butenes are recovered as 2-butene, reaction 1 is maximized and the selectivity to propylene maximized via reaction 1.

4. In the conventional flowsheet with isobutylene removal before the single metathesis reactor, the conversions are sensitive to the quantity of both ethylene and 1-butene which are present. The reaction of 2-butene with itself is nonproductive (not shown in Table A). If a CD DIB system is used at this point, the feed to metathesis is 2-butene. Under conditions of low ethylene and low 1-butene, the butenes conversion will be low as shown by the comparison of examples 1 and 2 where n-butene conversion dropped from 57 to 39%. This will result in increased recycles to achieve high butenes utilization. By using the process of the present invention, high butenes conversions are maintained even at low ethylene availability. To maximize conversions in the autometathesis step, the ratio of 2-butene to the sum of 1-butene and isobutylene should be between 0.5 and 1.5.

5. In a desire to keep conversions in the conventional prior art system high under conditions of low ethylene, a mixed bed catalyst system having some isomerization activity is used. This isomerizes the 2-butene back to 1-butene to allow reaction 2 to occur. A mixed bed catalyst system (metathesis and double bond isomerization catalysts) has been shown to be susceptible to butadiene poisoning under autometathesis or low ethylene conditions. Thus the selective hydrogenation unit (or the CD DIB) may be required to more fully convert butadiene and thus have losses to butanes by overhydrogenation. However, with a back end de-isobutyleneizer, the feed to the metathesis is a mixture of 2-butene plus 1-butene and isobutylene. The reaction of 2-butene with either of these butenes is fully productive and thus no isomerization activity is required and high conversions can be achieved (59% n-butenes in example 4 versus 39% in example 2). This allows operation with the $WO_3$ on silica metathesis catalyst only and thus allows a high butadiene

TABLE F

| | Feed to Automet 38 Kg/H | Automet Product Kg/H | Deethyleneizer Product 42 Kg/H | Propylene Product 44 Kg/H | $C_5 + 49$ Kg/H | Feed to Isobutylene Removal 50 Kg/H | Isobutylene Removed Kg/H | C4 Purge 54 Kg/H | Conventional Metathesis Feed 58 Kg/H | Conventional Metathesis Effluent 62 Kg/H |
|---|---|---|---|---|---|---|---|---|---|---|
| $C_2$ | 0.0 | 295.6 | 1902.1 | 1.7 | 0.0 | 0.0 | 0.0 | 0.0 | 2461.4 | 1608.2 |
| $C_3$ | 0.0 | 1910.5 | 2.9 | 4350.7 | 0.0 | 205.9 | 205.9 | 0.0 | 1.6 | 2649.0 |
| Inerts (Butane + Pentane) | 8557.6 | 8557.6 | 0.0 | 14.8 | 80.6 | 19589.4 | 5852.1 | 77.6 | 11127.3 | 11127.3 |
| n-$C_4$ | 6507.8 | 2679.2 | 0.0 | 2.4 | 7.0 | 3666.9 | 94.5 | 20.9 | 2893.6 | 997.0 |
| i-$C_4$ | 3416.0 | 1474.3 | 0.0 | 4.3 | 0.7 | 1590.3 | 1419.5 | 1.0 | 138.4 | 121.0 |
| BD | 143.4 | 143.4 | 0.0 | 0.3 | 0.1 | 155.2 | 140.2 | 0.1 | 12.2 | 12.2 |
| n-$C_5$ | 0.0 | 915.0 | 0.0 | 0.0 | 984.2 | 48.6 | 0.0 | 0.2 | 39.4 | 117.9 |
| i-$C_5$ | 0.0 | 1001.4 | 0.0 | 0.0 | 998.3 | 36.2 | 0.0 | 0.2 | 29.3 | 33.1 |
| n-$C_6$ | 0.0 | 187.5 | 0.0 | 0.0 | 203.3 | 0.0 | 0.0 | 0.0 | 0.0 | 15.8 |
| i-$C_6$ | 0.0 | 1460.2 | 0.0 | 0.0 | 1481.1 | 0.0 | 0.0 | 0.0 | 0.0 | 20.9 |
| $C_6+$ | 0.0 | 0.0 | 0.0 | 0.0 | 0.9 | 0.0 | 0.0 | 0.0 | 0.0 | 0.9 |
| SUM | 18624.8 | 18624.7 | 1904.9 | 4374.2 | 3756.2 | 25292.6 | 7712.1 | 100.0 | 16703.2 | 16703.2 | tolerance. The butadiene can be as much as 10,000 ppm in the fresh feed. The butadiene will not build up since it will be hydrogenated in the back end de-isobutyleneizer. Ultimately this processing scheme will increase the net butenes feed to metathesis.

6. In the reaction of butenes with themselves and to the extent that pentenes are formed, there is a loss in selectivity to propylene. In the conventional sequence in the reaction with ethylene, isobutylene must be rejected as a purge stream prior to metathesis since it does not react and would build up in the system under $C_4$ recycle conditions. To the extent that two normal butenes react with themselves in the metathesis reaction 2, 62.5 wt % of the normal butenes form pentanes and are lost to the production of propylene. Since the isobutylene is lost to purge prior to the reaction, it is more efficient to reject some of the iso-butylene as iso-pentenes in the autometathesis step of the present invention while both improving the selectivity of normal butenes to propylene and maximizing the normal butenes for reaction with ethylene.

The invention claimed is:

1. A process for the production of propylene from a $C_4$ olefin stream containing n-butenes, isobutylene and paraffins comprising the steps of:
   a. passing said $C_4$ olefin stream in contact with a metathesis catalyst whereby autometathesis occurs including the reaction of isobutylene with n-butenes and an autometathesis product is produced containing ethylene and propylene and heavier olefins including unreacted isobutylene and paraffins;
   b. fractionating said autometathesis product to remove an ethylene stream leaving a deethyleneized stream of said propylene and said heavier olefins and paraffins;
   c. fractionating said deethyleneized stream to remove propylene product leaving a depropyleneized stream of said heavier olefins and paraffins;
   d. processing said depropyleneized stream to remove isobutylene leaving a remaining $C_4$ and heavier olefins stream also containing paraffins;
   e. purging a portion of said remaining $C_4$ and heavier olefins stream to limit paraffin buildup;
   f. admixing the remaining portion of said remaining $C_4$ and heavier olefins stream with a quantity of ethylene sufficient for conventional metathesis wherein said quantity of ethylene comprises said removed ethylene stream and an amount of external fresh ethylene selected such that the molar ratio of said external fresh ethylene to the n-butenes in said $C_4$ olefin stream is from zero to 0.8; and
   g. passing said admixture in contact with a metathesis catalyst and reacting at least a portion of the $C_4$ and heavier olefins stream with ethylene to produce a metathesis product containing additional propylene.

2. A process as recited in claim 1 wherein said conventional metathesis product is combined with and fractionated with said autometathesis product.

3. A process as recited in claim 1 wherein said step d of removing isobutylene comprises a catalytic distillation hydroisomerization de-isobutyleneizer process wherein 1-butene is converted to 2-butene.

4. A process as recited in claim 1 wherein said $C_4$ olefin stream additionally contains butadiene limited to a level of less than 10,000 ppm.

5. A process as recited in claim 4 wherein said butadiene level is limited to a level of less than 500 ppm.

6. A process as recited in claim 1 where the autometathesis catalyst consists of a group VIA or VIIA metal oxide either supported or unsupported.

7. A process of claim 6 where the autometathesis catalyst is tungsten oxide on silica.

8. A process of claim 6 where the autometathesis catalyst is admixed with a Group IIA basic metal oxide double bond isomerization catalyst.

9. A process of claim 8 where the double bond isomerization catalyst is magnesium oxide.

10. A process as recited in claim 1 where the conventional metathesis catalyst consists of a group VIA or VIIA metal oxide either supported or unsupported.

11. A process of claim 10 where the conventional metathesis catalyst is tungsten oxide on silica.

12. A process of claim 10 where the conventional metathesis catalyst is admixed with a Group IIA basic metal oxide double bond isomerization catalyst.

13. A process of claim 12 where the double bond isomerization catalyst is magnesium oxide.

14. A process of claim 10 where the conventional metathesis catalyst is formulated to have both the metathesis reaction function and a double bond isomerization function.

15. A process for the production of propylene from a $C_4$ olefin stream containing n-butenes, isobutylene and paraffins comprising the steps of:
   a. passing said $C_4$ olefin stream in contact with a metathesis catalyst whereby autometathesis occurs including the reaction of isobutylene with n-butenes and an autometathesis product is produced containing ethylene and propylene and heavier olefins including unreacted isobutylene and paraffins;
   b. fractionating said autometathesis product to remove an ethylene stream leaving a deethyleneized stream of said propylene and said heavier olefins and paraffins;
   c. fractionating said deethyleneized stream to remove propylene product leaving a depropyleneized stream of said heavier olefins and paraffins;
   d. processing said depropyleneized stream to remove the $C_5$+ fraction leaving a mixed $C_4$ stream,
   e. processing said mixed $C_4$ stream to remove the isobutylene leaving a remaining normal $C_4$ olefins stream also containing paraffins;
   f. purging a portion of said remaining normal $C_4$ olefins stream to limit paraffin buildup;
   g. admixing the remaining portion of said remaining $C_4$ olefins stream with a quantity of ethylene sufficient for conventional metathesis wherein said quantity of ethylene comprises said removed ethylene stream and an amount of external fresh ethylene selected such that the molar ratio of said external fresh ethylene to the n-butenes in said $C_4$ olefin stream is from zero to 0.8; and
   h. passing said admixture in contact with a metathesis catalyst and reacting at least a portion of the $C_4$ olefins stream with ethylene to produce a metathesis product containing additional propylene.

16. A process as recited in claim 15 wherein said conventional metathesis product is combined with and fractionated with said autometathesis product.

17. A process as recited in claim 15 wherein said step e of removing isobutylene comprises a catalytic distillation hydroisomerization de-isobutyleneizer process wherein 1-butene is converted to 2-butene.

18. A process of claim 15 where the composition of said $C_4$ olefin stream is such that the ratio of 2-butene to the sum of 1-butene and isobutylene is 0.5 to 1.5.

19. A process as recited in claim 1, wherein at least half of the isobutylene is reacted with n-butenes during autometathesis.

20. A process as recited in claim 1, wherein, in autometathesis, the selectivity of propylene from the n-butenes is at least about 75%.

21. A process as recited in claim 15, wherein at least half of the isobutylene is reacted with n-butenes during autometathesis.

22. A process as recited in claim 15, wherein, in autometathesis, the selectivity of propylene from the n-butenes is at least about 75%.

* * * * *